April 15, 1958 H. D. DOUGHERTY Plant Pat. 1,696
PEACH TREE
Filed Feb. 25, 1957
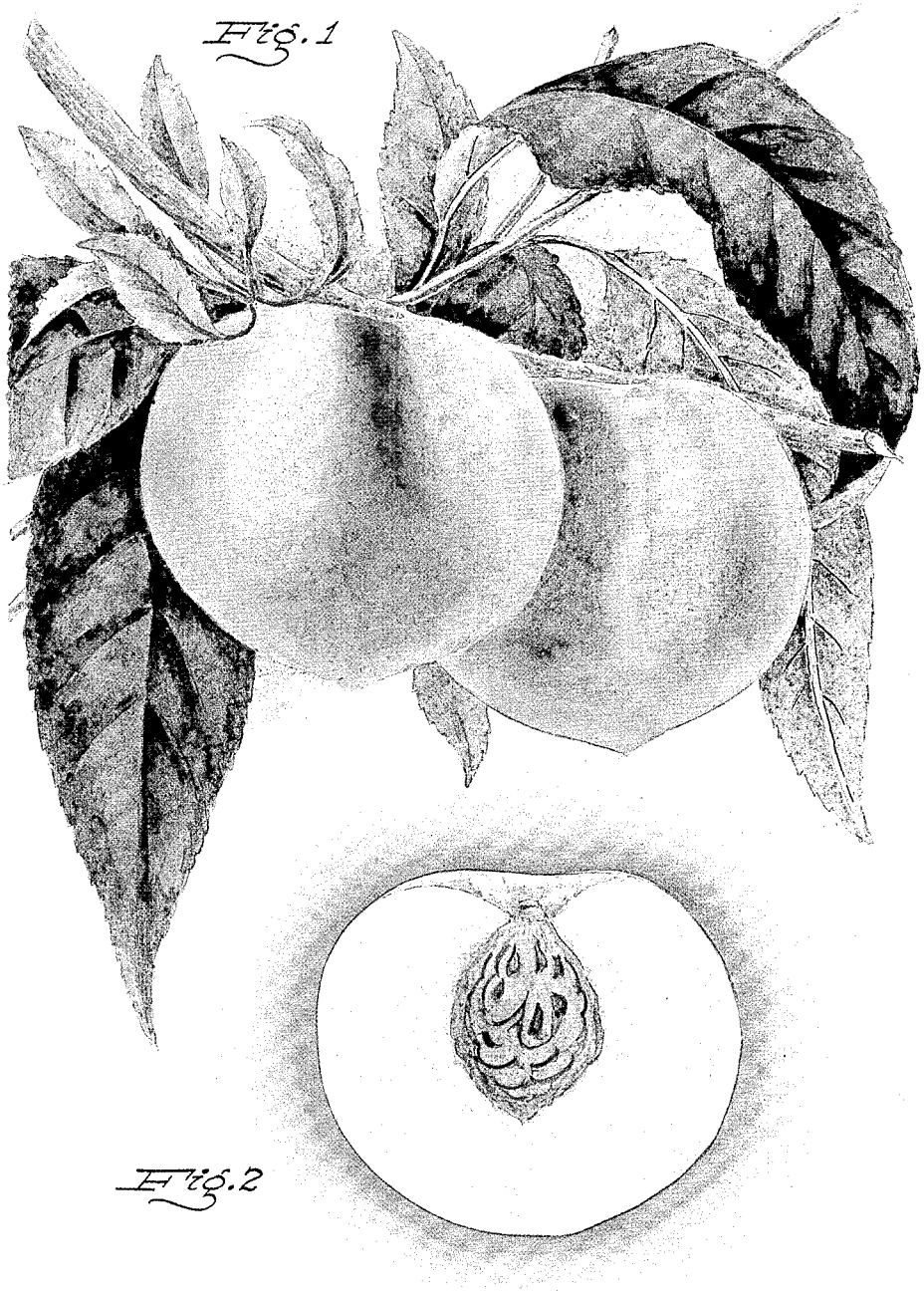
WITNESS
Addison E. Avery
INVENTOR
Harold H. Dougherty
Webster & Webster
ATTYS.

United States Patent Office

Plant Pat. 1,696
Patented Apr. 15, 1958

1,696

PEACH TREE

Harold D. Dougherty, Farmersville, Calif.

Application February 25, 1957, Serial No. 642,326

1 Claim. (Cl. 47—62)

This invention relates to a new and distinct variety of peach tree which bears large, attractive, freestone fruit having a relatively early ripening period and other desirable characteristics, as will hereinafter appear.

This variety may best be compared with the Hale Haven peach, and the Kim or July Elberta peach; being generally similar in growth, spread, and vigor of the tree, but substantially distinct with respect to the fruit, as follows:

The fruit of the present variety has skin quite tenacious to the flesh, and such skin is almost entirely overspread with a deeper red blush on a yellow ground color which shows through to a limited extent; i. e., in certain areas or streaks there is a gold flecked appearance.

Additionally, the yellow flesh of the fruit colors to a greater extent with orange or red mottling when the fruit is fully ripe, with a very conspicuous darker red at—and radiating from—the pit cavity.

As to configuration, the fruit of the present variety—on the average—does not have a pointed apex, is more rounded, and the suture is relatively inconspicuous. Further, the pistil point on some specimens remains a pinpoint of green even when the fruit is ripe to shipping stage, and the stone is at least as small, yet with a lower percentage of split pits.

The fruit of the present variety is—in addition to its large size, attractive appearance, and other characteristics above mentioned—characterized by excellent keeping and shipping qualities, both very desirable in a commercial peach.

This variety of peach tree was originated by me on my ranch at Farmersville, Tulare County, California, as one of a group of open-pollenated seedlings. The parentage of the variety is unknown, but is believed to be Hale Haven × Johnson Cling.

The variety was selected by me from said group of open-pollenated seedlings—for further observation and testing—because it evidenced outstanding vigor and leaf characteristics.

After its selection, and when the parent tree of the variety grew to maturity, the fruit was recognized as having novel characteristics and being of a high commercial quality.

I therefore initially asexually reproduced the variety on my ranch, located as aforesaid, by grafting scion wood from the parent tree onto seedling root stock, and these reproductions have—in maturity—remained true in all respects, as have other and subsequent asexual reproductions.

In the drawings:

Fig. 1 is an elevation showing two of the fruit, together with twigs and leaves.

Fig. 2 is a sectional elevation of one of the fruit detached, and with the stone exposed.

Referring now more particularly to the pomological details of this new and distinct variety of peach tree, the following is an outline description thereof; all major color plate identifications being by reference to Maerz and Paul Dictionary of Color:

Tree:
- *Size.*—Large.
- *Vigor.*—Vigorous.
- *Growth.*—Medium spreading.
- *Density.*—Medium.
- *Shape.*—Vase formed.
- *Hardiness.*—Hardy.
- *Production.*—Productive.
- *Bearing.*—Regular bearer.

Trunk:
- *Size.*—Medium.
- *Texture.*—Medium smooth.

Branches:
- *Size.*—Medium.
- *Texture.*—Smooth.
- *Color.*—Gray-green.
- *Lenticels.*—Medium number; medium size.

Leaves:
- *Size.*—Large. Average length, 7″. Average width, 2″. Maximum length, 9″. Maximum width, 2½″.
- *Shape.*—Oblanceolate; acutely pointed.
- *Thickness.*—Medium.
- *Texture.*—Smooth.
- *Margin.*—Crenate; finely serrate.
- *Petiole.*—Medium length; medium thickness.
- *Glands.*—Average number—two. Opposite; medium size; globose; reddish cast; positioned on base of leaf.
- *Stipules.*—Two at base of each leaf-stalk.
- *Color.*—Top side—medium dark green (23–L–6). Under side—lighter green (22–I–6).

Flower buds:
- *Hardiness.*—Hardy.
- *Size.*—Medium.
- *Length.*—Medium.
- *Shape.*—Conic; appressed.
- *Pubescence.*—Pubescent.

Flowers:
- *Blooming period.*—First bloom about March 2nd, and full bloom about March 5th in average season. Medium blooming period compared with other varieties.
- *Size.*—Large.
- *Color.*—Pink.

Fruit:
- *Maturity when described.*—Hard ripe (good eating but hard enough for good shipping).
- *Date of first picking.*—June 29th to July 10th.
- *Date of last picking.*—July 10th to July 15th.
- *Size.*—Large (averaging 95% large, 5% medium). Average diameter axially, 2¾″. Average diameter transversely in suture plane, 2½″.
- *Shape.*—Uniform; symmetrical; globose.
- *Suture.*—A shallow inconspicuous line with slight depression beyond pistil point.
- *Ventral surface.*—Rounded; strongly lipped; lips equal.
- *Cavity.*—Circular, with suture showing on one side. Average depth, 1½″. Average breadth, 15/16″. Markings—red.
- *Base.*—Rounded.
- *Apex.*—Short; depressed.
- *Pistil point.*—Oblique.

Skin:
- *Thickness.*—Thick.
- *Texture.*—Tough; tenacious to flesh.
- *Tendency to crack.*—Slight.

*Down.*—Scant; short.

*Color.*—Yellow ground color (11–L–8) almost entirely over-spread or blushed with a relatively dark red (3–K–11, shading to 7–L–6), with some areas darker red (56–L–12). The yellow ground color tends in certain areas to show through the red as gold flecks.

Flesh:

*Amygdalin.*—Moderate.

*Juice.*—Moderate; rich.

*Texture.*—Firm; meaty.

*Fibers.*—Few; fine; tender.

*Ripens.*—Evenly.

*Flavor.*—Mild.

*Aroma.*—Distinct.

*Eating quality.*—Best.

*Color.*—Yellow (9–J–3), mottled with orange (9–L–7) inwardly of the skin when fully ripe, and having a conspicuous darker red (1–K–9) at and radiating from the pit cavity. Yellow fibers at surface of pit cavity.

Stone:

*Type.*—Free; parts from flesh smoothly.

*Fibers.*—Medium length.

*Size.*—Medium. Average length, 1½″. Average breadth, 15/16″ to 1 1/16″. Average thickness, 11/16″.

*Form.*—Obovoid.

*Base.*—Straight.

*Hilum.*—Oval.

*Apex.*—Acute.

*Sides.*—Equal.

*Surface.*—Regularly furrowed toward apex; ridged toward apex; pitted toward base.

*Ridges.*—Rounded toward apex; on either side; interrupted.

*Pits.*—Elongated.

*Ventral edge.*—Thin.

*Dorsal edge.*—Narrow, with shallow groove toward base.

*Tendency to split.*—Slight.

*Color.*—Reddish cast (6–I–6).

Use: Local; dessert; canning; drying.

Keeping quality: Very good.

Shipping quality: Exceptionally good.

The previously existing peaches, herein mentioned, are believed unpatented, excepting the July Elberta, United States Plant Patent No. 15.

The tree and its fruit herein described may vary in slight detail due to climatic and soil conditions under which the variety may be grown.

The following is claimed:

A new and distinct variety of peach tree, as illustrated and described, characterized—in comparison with the Hale Haven and Johnson cling peach trees—by general similarity in growth, spread, and vigor; and—in distinction—by large, early ripening freestone fruit having skin which is tenacious to the flesh and almost entirely over-spread with a deeper red blush on yellow ground color, and yellow flesh which colors to a greater extent with orange or red mottling when fully ripe, with a conspicuously darker red at and radiating from the pit cavity; and—in further distinction—by fruit which has a more rounded shape, usually without a pointed apex, an inconspicuous suture, a pistil point which frequently remains green at shipping stage, a lower percentage of split pits, and excellent keeping and shipping qualities.

No references cited.